United States Patent [19]

Dick

[11] 4,409,984
[45] Oct. 18, 1983

[54] FM-DIGITAL CONVERTER

[75] Inventor: Joseph B. Dick, Earlysville, Va.

[73] Assignee: General Electric Company, Schenectady, N.Y.

[21] Appl. No.: 237,821

[22] Filed: Feb. 25, 1981

[51] Int. Cl.³ .............................................. A61B 5/04
[52] U.S. Cl. .................................................. 128/696
[58] Field of Search .................. 328/140, 141, 220 R; 340/347; 364/417; 128/630, 696, 697, 903, 904

[56] References Cited

U.S. PATENT DOCUMENTS

| | | | |
|---|---|---|---|
| 2,405,597 | 8/1946 | Miller . | |
| 3,499,124 | 3/1970 | Wortzman | 128/696 |
| 3,617,885 | 11/1971 | Wheable | 340/347 AD |
| 3,909,599 | 9/1975 | Trott, Jr. et al. | 235/151.3 |
| 4,027,146 | 5/1977 | Gilmore | 235/151.31 |
| 4,039,806 | 8/1977 | Fredriksson et al. | 340/347 AD |
| 4,281,664 | 8/1981 | Duggan | 128/696 |

Primary Examiner—William E. Kamm
Attorney, Agent, or Firm—Wheeler, House, Fuller & Hohenfeldt

[57] ABSTRACT

A square pulse wave is frequency modulated (FM) by an input analog voltage that represents a physiological parameter such as an electrocardiograph waveform. A binary counter is initiated for counting a predetermined integral number, such as four, FM periods for each FM wave sampling interval. A counter/timer counts high rate clock pulses during the interval and stops when the predetermined number of FM periods is counted, thereby producing a count that is proportional to the time per FM period or cycle. The reciprocal of time is calculated to produce a digital number that is proportional to frequency and, hence, to the instant amplitude of the analog input voltage. The number constitutes address to a look-up table storing digital words that correspond in value to dc voltages.

4 Claims, 2 Drawing Figures

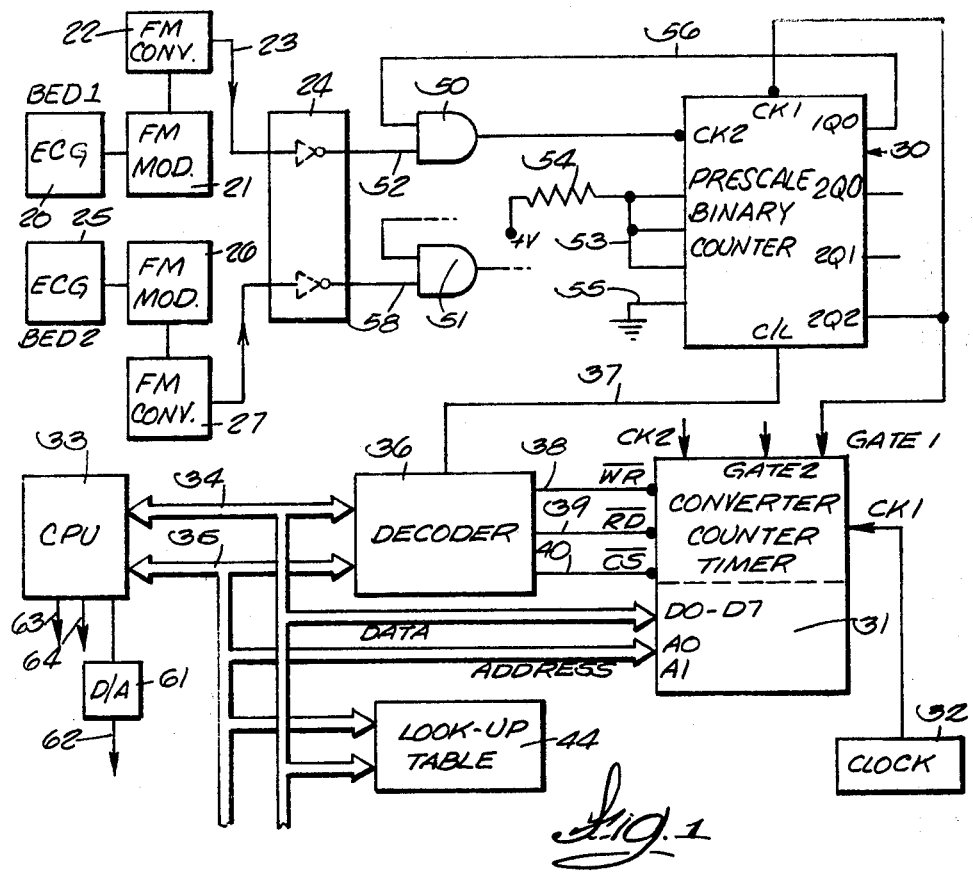
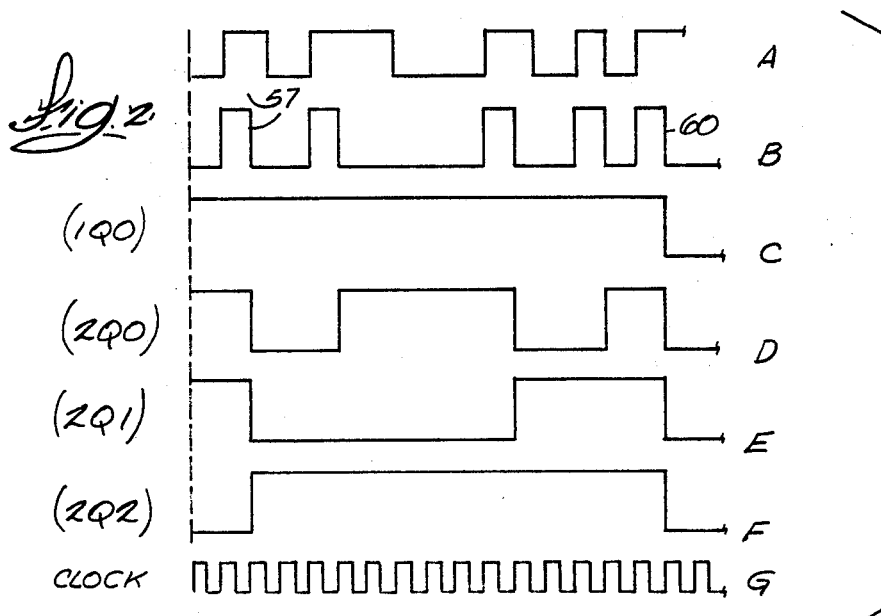

4,409,984

FM-DIGITAL CONVERTER

BACKGROUND OF THE INVENTION

This invention relates to a system for acquiring data from a plurality of sources simultaneously.

The invention was developed for use in a physiological data acquisition system but it has many other applications as well.

A typical use of the invention is in connection with cardiac monitoring of a plurality of bedridden patients in a cardiac care unit. In such cases it is customary to transmit electrocardiograph (ECG) data to a central station processor for determining if the heart is exhibiting arrhythmia or other abnormalities. One use of the signals is to display the analog ECG on a cathode ray oscilloscope along with ECG waveforms of other patients.

It is known in the prior art to use the analog ECG signals derived from the patient to frequency modulate (FM) a carrier wave for transmitting the ECG values to the central monitoring station. At the monitoring station, it is necessary, on some occasions, to demodulate the FM signals and convert to digital or analog equivalents of the original analog ECG or whatever physiological parameter is being monitored. In some installations, dozens of patients must be monitored at a central station simultaneously. The conventional approach was to demodulate the respective FM signals and then perform an analog-to-digital conversion. The disadvantage of this approach is that dozens of demodulators may be required in order to supply enough data to meet the required digital data rate. Moreover, a plurality of multiplexers are required to switch the demodulated FM to the analog-to-digital (A/D) converter. This approach requires a large amount of circuit board area which is obviously disadvantageous. Moreover, adjustment of the demodulators is difficult and repeatability from unit to unit is often unreliable.

A further disadvantage of the foregoing and other prior art approaches is that one or more rather costly A/D converters must be used or time-shared.

SUMMARY OF THE INVENTION

The present invention overcomes the above-noted disadvantages of prior art systems and, furthermore, obviates the need for using an A/D converter to obtain a digital representation of an analog siganl such as an ECG signal or other analog physiological parameter originating at a patient.

In accordance with the invention, a microprocessor is used to control data acquisition timing although, it should be understood, that almost any central processor unit (CPU) could be used.

Briefly stated, in accordance with the invention, a high-speed clock, such as a 1.33 MHz clock is counted for a predetermined number of periods of the incoming FM signals by a counter/timer chip under processor control. The suggested FM frequency used herein is in the range of 1200 Hz to 1900 Hz. Higher FM frequency could be measured if the clock frequency were increased but accuracy diminishes. There is never any ambiguity in the number of FM pulses within a counting window because, in the present invention, the FM pulse counter always begins and ends counting on the first and last negative going parts of an FM cycle. This results in a finite number of clock pulses being counted without having to be concerned with starting to count at zero crossing. The clock pulse count value is then related to a digital value representing an analog value in a look-up table that is scanned by the microprocessor. This look-up value is related to the analog value that was originally encoded in the FM signal from the bedside. Hence, a digital representation of an analog value becomes available without having to go through an A/D converter and a reconstruction of the original analog signal becomes available too.

A more detailed description of the new system for converting an FM signal which has been modulated by an analog voltage to digital data representing the analog signal amplitudes and then converting back to analog form will now be described in greater detail in reference to the drawing.

DESCRIPTION OF THE DRAWING

FIG. 1 is a block diagram of the new converter system; and

FIG. 2 shown the timing diagrams which are useful for explaining operation of the system.

DESCRIPTION OF A PREFERRED EMBODIMENT

FIG. 1 will be used primarily to describe how one of the data channels among a plurality of channels operates. In the upper left, a block marked 20 represents a physiological parameter sensor, such as an electrocardiograph or ECG at one of the bedsides. This device outputs a typical analog ECG waveform to an FM modulator represented by the block 21. The output of modulator 21 is a train of square wave pulses that have been frequency modulated by the ECG analog input voltage such that the frequency within any time interval corresponds to the present magnitude of the modulating analog voltage. In an actual embodiment, the output of modulator 21 is a 50% duty cycle of the FM. A modulated FM waveform having a 50% duty cycle is typified in part A of FIG. 2. The output of modulator 21 is input to a converter represented by the block 22. Converter 22 converts the 50% duty cycle FM waveform to a constant pulse width variable duty cycle output pulse train such as is illustrated in part B of FIG. 2. This FM pulse train is conducted from bedside to the central patient monitoring station by a cable 23 where it becomes input to a buffer 24. The buffer is comprised of a plurality of inverters, two of which are shown.

In an actual embodiment a quad buffer 24 is used and it handles FM data from a total of four separate bedsides. Only one additional FM signal input to buffer 24 is shown in this example. Its FM input signal results from an ECG 25 at another bedside driving an FM modulator 26 followed by an FM converter 27 whose output is sent to an inverter in buffer 24. Modulator 26 and converter 27 in the front end of the second channel perform the same functions as previously described modulator 21 and converter 22 in the first channel. Since all data channels are basically the same, only one of them will be described in detail.

Two major components of the FM to digital data conversion system are a presettable binary counter 30, called a prescale, and a counter/timer 31 which is basically a converter as used herein. The output of a stable crystal controlled clock 32 is one input to counter/timer 31. The clock frequency should be substantially higher than the FM frequency. By way of example and not limitation, a 1.33 MHz clock is used in a commercial embodiment and the FM frequency range is 1200 Hz to 1900 Hz. With the system described herein a one Hz variation in FM frequency can be discerned which means that conversion is very accurate. As implied earlier, counter/timer 31 counts the number of clock pulses that occur during a definitely known predetermined integral number of variable duty cycle FM waveform periods. The number of FM periods during which clock pulses are to be counted is determined by the presettable or programmable binary counter 30. By way of illustration, in an actual embodiment, the counter/timer 31 counts for the duration of four FM periods which are determined by binary counter 30. In an actual embodiment, a type 74197 integrated circuit binary counter 30 is used and a type 8253 integrated circuit counter/timer 31 is used. This type of counter/timer 31 happens to have three independent 16-bit counters but only two were used for FM conversion. Thus, with this particular arrangement, the counter/timer 31 is required for every two FM data conversion channels.

Another main component of the system is a microprocessor-based CPU represented by the block marked 33. It provides all controls timing and calculations for the system. Block 33 symbolizes the usual components of a CPU, that is, arithmetic and control units, memory or program storage and operations, and input and output ports. The data bus for the system is marked 34 and the address bus is marked 35. These buses will be understood to also lead to the components for other FM conversion channels. It will be evident that a single microprocessor-based CPU 33 is used to control many channels. In one actual embodiment by way of example, thirty-two individual FM data channels at the central monitoring station are controlled by a single microprocessor.

Another major component of the FIG. 1 system is a decoder symbolized by the block marked 36. Under CPU control, it provides a signal by way of line 37 to the count/load (C/L) pin of the binary counter 30 to initialize it as will be explained in further detail shortly hereinafter. Initialization in this case means setting the counter 30 for counting a predetermined integral number of FM cycles, such as four cycles, for reasons that will be discussed. Decoder 36 also provides a signal by way of line 38 ($\overline{WR}$) which starts the selected 16-bit counter within counter/timer 31 to begin counting for the duration of four FM periods. Another line 39 provides the signal ($\overline{RD}$) to enable the CPU 33 to read out the number of clock pulse counts from the selected counter in counter/timer 31 that occurred during the four FM periods. The clock pulse counts per four FM cycles are read out by the CPU 33 for each FM sample in each channel repeatedly. The other line 40 from decoder 36 is the chip-select ($\overline{CS}$) line. It is switched high or low in accordance with the 16-bit counter that is to be selected in the counter/timer 31 for the particular FM data being converted.

The system determines the number of clock pulses counted by counter/timer 31 per FM period which is a measure of time. The reciprocal of time corresponds to FM frequency. The FM frequency corresponds to the instantaneous magnitude of the analog ECG waveform that is modulating the FM carrier. CPU 33 obtains the counts from the counter/timer 31 for successive samples of the FM waveforms in all of the channels and is involved in bringing about a conversion of the count data for each sample to a digital number representative of the original analog value.

The counter/timer chips 31 are all coupled to the CPU data bus 34 and address bus 35. Two address lines, $A_0$ and $A_1$, are used with the counter/timer chips 31 as indicated on them. The CPU addresses the counter/timer chip for selecting which of the two internal 16-bit counters at the sampling time. At the beginning of each sampling or FM to digital conversion cycle the CPU provides the data for setting one and the other of the 16-bit counters to zero. The clock pulse count is retrieved by the CPU at the end of each sampling interval in two 6-bit bytes, in this particular design, from data pins $D_0$–$D_7$ on counter/timer 31.

Another principal component of the FIG. 1 system is a look-up table (LUT) symbolized by the block marked 44. The LUT has a table of digital values in it which correspond to a series of analog voltages. The CPU uses the clock pulse count from counter/timer 31 obtained during occurrence of 4 FM periods as an address to the LUT which responds by providing a digital value over data bus 34 to the CPU. This digital value corresponds to the ECG analog dc voltage magnitude at the instant of sampling. Of course sampling occurs at such a high rate that digital data for reconstruction of a continuous analog voltage are obtained. In an actual embodiment the LUT provides 240 samples per second by way of example. This is more than adequately fast in view of the fundamental frequency of a typical ECG waveform being about 10 Hz.

Another significant component in each channel of the system is an AND gate such as the one marked 50 near the top of FIG. 1. When a quad buffer 24 is used, there will be a total of four FM input signals and gates. Only one more gate is illustrated and it is marked 51.

The manner in which the various components in FIG. 1 cooperate to effect conversion of th FM ECG signal to digital values will now be described in greater detail in reference to FIG. 1.

As indicated earlier, the variable duty cycle FM signal coming in from converter 22 is input to an inverter in buffer 24. The variable duty cycle waveform is represented by part B of FIG. 2. This waveform is input to AND gate 50. At time t=0, decoder 36, in response to a timing signal from the CPU 33, initializes the outputs 1Q0, 2Q0, 2Q1 and 2Q2 of binary counter 30 to a predetermined state. This is done by asserting the proper signal on the C/L (count/load) pin of binary counter 30 by way of line 37 from decoder 36.

Now looking at counter/timer 31, it, as has been mentioned, contains at least two 16-bit counters. One counter is used for bed or patient number 1 FM data and the other is for patient number 2 FM data. Counter/timer 31 is programmable which means that the system's software can load a predetermined binary value into the counter register. Initially, that is, at the beginning of a conversion cycle, CPU 33 clears counter/timer 31 by loading all zeroes into its respective registers. Of course, the particular chip must first be selected by decoder 36 under CPU control befodre the CPU can initially clear the counter 31. The decoder 36 selects counter 31 by asserting $\overline{CS}$ low by way of line 40. Next, the CPU 33 provides an address to counter/timer 31 to select which of the internal counters will be loaded with zeroes. As previously indicated, address lines $A_0$ and $A_1$ select the proper internal counter of counter/timer 31. After the particular counter is selected, the decoder 36 then asserts the RD pin low so that the CPU can load the counter register by way of data bus 34 with zeroes to initially clear the counter.

When CPU 33 clears the counter, it also presets the output of the prescale or presettable binary counter 30 to a particular state for permitting four FM periods to be determined. The output pins of binary counter 30 are marked, respectively, 2Q0, 1Q1, 2Q1 and 2Q2. Their initial states are exhibited in parts C, D, E and F, respectively, in the FIG. 2 timing diagram where these parts are marked in correspondence with the output pins of binary counter 30 to which they relate. As can be seen in FIG. 2, the outputs of binary counter 30 ae preset to a HIGH (1Q0), HIGH (2Q0), HIGH (2Q1), and LOW (2Q2) when decoder 36 pulls the C/L pin of binary counter 30 low. Three of the inputs 53 to presettable binary counter 30 are tied high through a pull-up resistor 54 leading to a voltage source and one input 55 is tied low. Therefore, when the C/L pin of counter 30 is pulled low, the corresponding outputs of counter 30 agree with the data inputs. The starting states of the various counter 30 outputs, as has been indicated, are also shown in the part C-F waveforms of FIG. 2. Thus, so far the bed or patient 1 counter in the converter or counter/timer 31 has been cleared by loading its register with all zeroes and the output of binary counter 30 has been set to a particular state for the beginning of every one of the closely successive FM sampling intervals.

The actual FM-to-digital conversion process will now be discussed. The initially high 1Q0 output of counter 30 shown in part C of FIG. 2 is fed by way of line 56 to an input of AND gate 50 as shown in FIG. 1. This action allows the FM data in one channel to be gated through AND gate 50 to the clock 2 (CK2) input of binary counter 30. As can be seen in FIG. 2, the first negative-going edge 57 of the FM pulse train in part B of FIG. 2, clocks the 2Q0, 2Q1 and 2Q2 outputs of binary counter 30 for four FM periods terminating with the negative-going edge 60 of the fourth FM cycle. Triggering with negative-going edges assures that there will be an integral number of full FM periods during a measuring time interval. As suggested in part G of FIG. 2, a substantial number of 1.33 MHz clock pulses are counted within the four FM periods. Roughly, by way of example, the ratio of clock pulses to FM periods might be 1000:1. After the 2Q2 output of counter 30 is high for four periods, this high output from 2Q2 is fed to gate 1 of counter/timer 31 which allows it to start decrementing in accordance with the 1.33 MHz clock input CK1 in this case. When the 2Q2 output of counter 30 goes low with the negative-going part of the last FM pulse in a sample, counter/timer 31 stops counting clock pulses. Every 4 ms CPU 33 initiates an interrupt, under software control, so it can read the digital values stored in counter/timer 31 by way of data bus 34. An interrupt time, decoder 36 pulls the read ($\overline{RD}$) pin of counter/timer 3 low so the count data can be read from counter/timer 31. The digital value in counter/timer 31 is then placed on the data bus for the CPU to obtain it for addressinng the LUT 44.

The digital value in counter/timer 31 for the four FM period count, is proportional to the number of 1.33 MHz pulses counted during the time window provided by the 2Q2 output of binary counter 30 which window is, of course, four FM periods long in this example. Since the width of the window is proportional to the FM period and the FM period is proportional to the ECG dc value, the number of 1.33 MHz clock pulses occurring during the window is proportional to the ECG dc value.

In general terms, the frequency f of the FM signal (proportional to the analog signal derived from the patient) is represented by the following equation:

$$f = N \times (MHz/C)$$

where N is the number of FM periods set by prescaler of counter 30, MHZ is the pulse rate of clock 32 and C is the number of clock pulses counted within the chosen number of FM periods.

The digital values, derived from the LUT, by the CPU, representing the successive magnitudes of the analog ECG signal in each channel can be converted from digital to analog waveform again for use at the central station. One digital-to-analog (D/A) converter is symbolized by the block 61 next to the CPU. In the actual system there is a D/A converter for each ECG channel. The analog outputs 62 from the illustrated and other converters can be used to drive a cathode ray tube, not shown, which displays one or more of the reconstructed ECG waveforms so that the heart conditions of several patients can be observed at the central station.

In the actual system, the CPU is programmed to use the digitized ECG waveform data to analyze the ECG to determine, for instance, heart rate, or the width of the QRS complex of the R-wave or occurrence of premature ventricular contractions and to provide alarm signals on outputs of the CPU such as those marked 61 and 62 if certain conditions are detected or go out of acceptable limits.

Now that the FM-to-digital conversion of the physiological data from one of the patients has been described, it will be evident that another data channel can be handled through the second part of counter/timer 31 if another binary counter such as the one marked 30 is added. In such case, the FM signal, based on using an analog ECG signal from electrocardiograph 25 is fed through quad buffer 24 and becomes input on line 58 to another AND gate 51. This AND gate would be connected to another binary counter, not shown but equivalent to counter 30, whose output would be coupled to the gate 2 input of counter/timer 31. The CK2 input to counter/timer 31 is indicated by an arrowheaded line at the top of the counter and is driven by the 1.33 MHz clock. Since counter/timer 31 has at least two 16-bit counters in it, one can be used for one FM channel and the other for another FM channel. CPU 33 simply regulates the decoder 36 to write and read into and out of the counter 31 at the proper time for each channel and alternately addresses the counter/timer 31 on address lines $A_0$ and $A_1$ to extract the counts representing the digital values by way of data bus 34.

For the purposes of presenting a practical example, the duration of four FM cycles or periods was determined by having binary counter 30 make four counts while the duration was being determined by counting 1.33 MHz clock pulses in counter 31. It will be understood, however, that more than four FM periods could be used and a higher or lower clock pulse rate could be used. In any case the number of FM periods and the clock pulse rate will be chosen to obtain the required fidelity between the original analog ECG waveform voltage and the final analog voltage resulting from the transformation from original analog to FM to digital to final analog.

Although the basic concepts of analog-to-FM-to-digital-to-analog conversion without using an A/D converter have been discussed in detail, it will be evident to those skilled in the art that the concepts may be variously implemented. Consequently, the true scope of the invention is to be determined only by interpreting the claims which follow.

I claim:

1. A multiple channel system for converting successive samples of analog input voltages for each channel to binary digital representations of the samples, respectively, where said analog voltages are represented, respectively, by frequency modulated (FM) signal trains comprised of substantially square wave cycles, said system comprising:

a gate having input and output means, one of said FM trains being fed to the input means of the gate, a binary counter having input and output means, the output means of the gate being coupled to the input means of the counter, means for initializing the counter at the beginning of each in a succession of FM signal sampling intervals, said counter responding to initialization by enabling the gate to feed the FM signal to said input means of the counter, said counter being operative to count a predetermined number of FM cycles and to disable the gate simultaneously with said number being counted to thereby terminate the sampling intervals, a clock pulse generator for generating a train of pulses at a frequency substantially higher than the FM signal frequency, counter/timer means having input means for the train of clock pulses and having output means for the binary digital numbers representing the number of clock pulses counted during each sampling interval, said counter/timer means responding to occurrence of said binary counter initialization by simultaneously beginning to count clock pulses and responding to occurrence of said predetermined number of FM cycles having been counted by terminating clock pulse counting, the binary number representative of the number of clock pulses counted during said number of FM cycles corresponding to the FM frequency during said sampling interval, means for converting the numbers corresponding to FM frequency to binary digital values corresponding to the amplitude of the aforesaid analog input voltage during each FM signal sample.

2. The system as in claim 1 wherein said means for converting the numbers comprises a look-up table having a plurality of addressable locations respectively storing digital data corresponding to analog dc voltage values, said look-up table having address input means and digital data output means, said binary digital numbers corresponding to FM frequency constituting addresses to said look-up table digital data locations, input of an address to said table resulting in output of digital data corresponding to an analog voltage value.

3. The system in any of claims 1 or 2 wherein:

said binary counter is set to count four FM cycles per sample of the FM signal train and the frequency of the clock pulses counted by said counter/timer is about 1.33 MHz.

4. Means for converting a train of frequency modulated (FM) pulse signals, whose frequency variations are representative of variations in the magnitude of an electrocardiograph (ECG) analog voltage used to modulate the signals, to digital numbers corresponding in value to the magnitude of the analog voltage waveform prevailing at times the FM signals are sampled, comprising:

a gate having one input for said train of FM pulses, an input for a gating signal and an output for the FM pulse train, a first edge triggered counter means having an input for the gated FM pulse train, one output coupled to said gating signal input and another output, said counter responding to being initialized by providing said gating signal and responding to counting a predetermined number of FM pulses by terminating said gating signal, said counter further responding to being triggered by an edge of the first FM pulse sample to be counted by setting said other output to one state and responding to the corresponding edge of the last FM in the sample by changing said output to another state, second counter means having input means for a clock pulse train whose frequency is substantially higher than the FM pulse frequency, and having a gate signal input coupled to said other output of said first counter means for enabling said second counter to begin counting clock pulses when said other output is set to said one state and for terminating counting in response to said other output changing to its other state, processor means and a data bus and an address bus coupled thereto, decoder means coupled to said data and address buses and having a plurality of output means coupled to said first counter means and said second counter means, respectively, said second counter means also being coupled to said address and data buses, and a look-up table coupled to said address and data buses, said look-up table storing digital data in addressable locations corresponding in value, respectively, to digitized analog voltage values, said decoder responding to a signal from said processor to start a sampling interval by initializing said first counter means and enabling said second counter to count clock pulses during the sampling interval as determined by occurrence of the corresponding edge of the last in said predetermined number of FM pulses in a sampling interval, the digital count in said second counter at the end of the sample corresponding to FM pulse frequency and, hence, to the analog input voltage magnitude during each sampling interval, said digital counts being read by said processor means by way of said data bus, and said processor means, using said count as an address to a look-up table location for obtaining a digital value corresponding to the FM pulse frequency and the analog input voltage during the respective sampling intervals.

* * * * *